United States Patent [19]

Richardson et al.

[11] Patent Number: 5,001,133
[45] Date of Patent: Mar. 19, 1991

[54] BENZOIC ACID DERIVATIVES

[75] Inventors: Brian P. Richardson, Magden, Switzerland; Günter Engel, Weil, Fed. Rep. of Germany; Rudolf K. A. Giger, Riehen; Andrea Vasella, Meilen, both of Switzerland

[73] Assignee: Sandoz Ltd., Basle, Switzerland

[21] Appl. No.: 267,062

[22] Filed: Nov. 4, 1988

Related U.S. Application Data

[63] Continuation of Ser. No. 882,807, Jul. 7, 1986, abandoned, which is a continuation of Ser. No. 683,380, Dec. 19, 1984, abandoned.

[30] Foreign Application Priority Data

Dec. 23, 1983 [CH] Switzerland ............ 6876/83
Dec. 23, 1983 [CH] Switzerland ............ 6879/83

[51] Int. Cl.$^5$ ............ A61K 31/46; C07D 401/12
[52] U.S. Cl. ............ 514/304; 514/413; 546/126; 548/455
[58] Field of Search ............ 546/124, 126, 128, 112, 546/183; 514/299, 304, 413; 548/455

[56] References Cited

U.S. PATENT DOCUMENTS

| | | | |
|---|---|---|---|
| 2,748,134 | 5/1956 | Stoll et al. | 546/193 |
| 3,170,927 | 2/1965 | Nador et al. | 546/129 |
| 3,177,252 | 4/1965 | Thominet | 564/167 |
| 3,342,826 | 9/1967 | Miller et al. | 546/224 |
| 3,405,134 | 10/1968 | Judd | 546/137 |
| 3,662,070 | 5/1972 | Thominet | 514/414 |
| 3,702,324 | 11/1972 | Skinner et al. | 546/133 |
| 4,093,734 | 6/1978 | Kruger et al. | 544/165 |
| 4,148,895 | 4/1979 | Lattrell et al. | 544/144 |
| 4,213,983 | 7/1980 | Hadley et al. | 546/95 |
| 4,273,778 | 6/1981 | Hadley et al. | 546/112 |
| 4,459,300 | 7/1984 | Watts | 546/112 |
| 4,499,099 | 2/1985 | Watts | 546/112 |
| 4,789,673 | 12/1988 | Donatsch et al. | 514/304 |
| 4,797,406 | 1/1989 | Richardson et al. | 546/183 |
| 4,803,199 | 2/1989 | Donatsch et al. | 514/304 |

FOREIGN PATENT DOCUMENTS

| | | |
|---|---|---|
| 701023 | 10/1966 | Belgium . |
| 849627 | 6/1977 | Belgium . |
| 42705 | 12/1981 | European Pat. Off. . |
| 67770 | 12/1982 | European Pat. Off. . |
| 68700 | 1/1983 | European Pat. Off. . |
| 76755 | 4/1983 | European Pat. Off. . |
| 765924 | 4/1983 | European Pat. Off. . |
| 13138 | 12/1983 | European Pat. Off. . |
| 94742 | 12/1983 | European Pat. Off. . |
| 2434547 | 1/1976 | Fed. Rep. of Germany . |
| 2557341 | 6/1977 | Fed. Rep. of Germany . |
| 2557342 | 6/1977 | Fed. Rep. of Germany . |
| 2803651 | 8/1978 | Fed. Rep. of Germany . |
| 6807287 | 11/1968 | Netherlands . |
| 774858 | 5/1957 | United Kingdom . |
| 1566307 | 4/1980 | United Kingdom . |
| 2042522 | 9/1980 | United Kingdom . |
| 2088364 | 6/1982 | United Kingdom . |
| 84/03281 | 8/1984 | World Int. Prop. O. . |

OTHER PUBLICATIONS

P. Donatsch et al., Chem. Abst., vol. 100, No. 209629q (1984).
J. Fozard, Advances in Neurology, vol. 33, pp. 295-307 (1982).
J. Hughes, Med. J. Australia, vol. 2, No. 17, p. 580 (1977).
J. Waters, Jour. of Med. Chemistry, vol. 21, No. 7, pp. 628-633 (1978).
C. Cheng et al., Jour. of Med. Chemistry, vol. 25, No. 2, pp. 145-152 (1981).
Hoppe-Seyler's Z. Physiol Chem. pp. 768-774, (1967).
Singh, et al. (J. Heterocyclic Chem., vol. 16, pp. 625-631, (1979).
Pharm. Zeit., No. 40, pp. 1455 and 1456 (1972).
Derwent Abstract 0006591 (1963).
E. Kasztreiner et al; Acta Chim. Acad. Scien., vol. 51, pp. 327-338 (1967).
Izv. Akad. Nauk. Arm. SSR, Biol. Nauk, vol. 15, No. 12, pp. 3-14 (1962) (corr. Chem. Abs. 5b65g).
O. Feher et al., Acta Biologica Szeged, vol. 21, pp. 113-125 (1975) Chem. Abs. 83522w (1976).
J. Bosse et al., Naunyn-Schmiedebergs Arch. Pharmacol. Exp. Path., vol. 259, pp. 34-44 (1967).
H. House et al., J. of Org. Chem., vol. 31, pp. 3482-3489 (1966).
E. Ohki et al., Chem. Pharm. Bull., vol. 18, No. 10, pp. 2050-2057 (1970).
E. Mikhlina et al., Khim.-Farm. Zh., vol. 7, No. 8, pp. 492-496 (1973).
H. Lieberman et al., J. of Pharm. Sciences, vol. 57, pp. 684 and 685 (1968).
E. Mikhlina, Chem. Abs. vol. 54, No. 22632h (1960).
J. Fozard et al., Proceedings of the B.P.S., pp. 499 and 500 (Sep. 7th-9th, 1977).

*Primary Examiner*—Mary E. Ceperley
*Attorney, Agent, or Firm*—Gerald D. Sharkin; Robert S. Honor; Joseph J. Borovian

[57] ABSTRACT

The substituted benzoic acid heterocyclic amides and esters are serotonin M antagonists. Included are compounds of the formula Iq

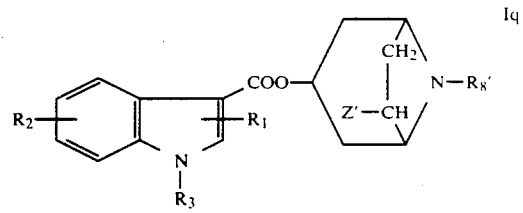

wherein $R_1$, $R_2$, $R_3$, $Z'$ and $R_8'$ have various definitions.

6 Claims, No Drawings

BENZOIC ACID DERIVATIVES

This is a continuation of application Ser. No. 06/882,807, filed July 7, 1986 which in turn is a continuation of application Ser. No. 06/683,380, filed Dec. 19, 1984, both now abandoned.

This invention relates to benzoic acid derivatives. It has been proposed (see for example J.R.Fozard in Advances in Neurology Vol. 33 Raven Press New York 1982) to use compounds with serotonin antagonistic effects, i.e. 5HT blocking effects in the treatment of migraine. Particularly interesting are the compounds which antagonise the 5-HT M-receptors. A particular active compound :f this type is Metoclopramide (U.S. Pat. No. 3177252) which J. B. Hughes in Med.J.Australia 2 No. 17. p.580 (1977) has reported to lead to an immediate beneficial effect on a migraine attack on slow i.v. injection of 10 mg.

Subsequently further compounds with serotonin-M antagonistic effect have been described. European Publication 67770 describes a narrow class of tropane phenyl esters.

The present invention provides a new group of compounds which has not been specifically suggested before in the literature and which have particularly interesting pharmacological properties, for example, serotonin M antagonistic activity and antiarrhythmic agents, e.g. as indicated by potency in the vagus nerve test mentioned hereinafter.

The present invention provides in one aspect compounds of formula I

A—CO—B—D     I wherein A is a group of formula II or III

    II

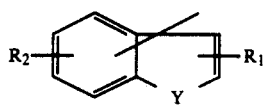
    III

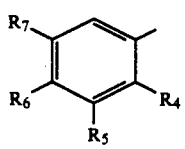

wherein
the free valence is attached to either fused ring in formula II,
Y is —CH$_2$—, —NR$_3$—, —O—, or —S—,
R$_1$ and R$_2$ are independently hydrogen, halogen, (C$_{1-4}$)alkyl, (C$_{1-4}$)alkoxy, hydroxy, amino, (C$_{1-4}$)alkylamino, di(C$_{1-4}$)alkylamino, mercapto or (C$_{1-4}$)alkylthio,
R$_3$ is hydrogen:(C$_{1-4}$)alkyl, (C$_{3-5}$)alkenyl, aryl or arylalkyl,
R$_4$ to R$_7$ are independently hydrogen, amino, nitro, (C$_{1-4}$)alkylamino, di(C$_{1-4}$)alkylamino, halogen, (C$_{1-4}$)alkoxy, (C$_{1-4}$)alkyl, (C$_{1-4}$)alkanoylamino or pyrrolyl,
B is —O' or —NHD—, and
is a group of formula

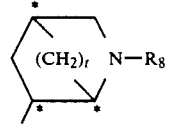
    IV

    V

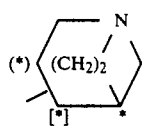
    VI

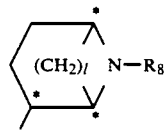
    VII wherein t is 1 or 2,

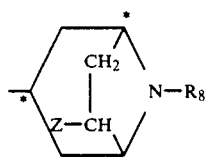
    VIII

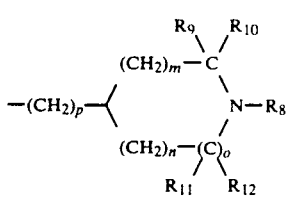
    IX wherein the bond is in the position 3 (*) or 4 [*],

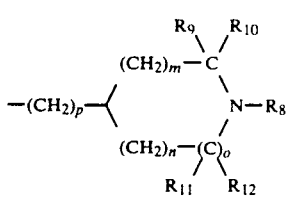
    X wherein 1 is 2 or 3,

XI wherein Z is (C$_{1-4}$)alkoxy, or

XII wherein $R_9$ to $R_{12}$ are independently hydrogen or $(C_{1-4})$alkyl,
m is 0, 1 or 2 and
n, o, p independently are 0 or 1,
wherein $R_8$ in each of formulae V to VII and X to XII is hydrogen, $(C_{1-7})$alkyl, $(C_{3-5})$alkenyl or aralkyl with the provisos that (1) when A is a group of formula III, and B is —NH—, then either D is a group of formula IV or $R_6$ is amino, $(C_{1-4})$alkylamino or di(alkyl$(C_{1-4})$amino and D is a group of formula XII other than 4-piperidinyl substituted by $R_8$ as defined above, (2) when A is a group of formula III, and B is —O—, then D is other than a group of formula XII which is piperidinyl, pyrrolidinyl, pyrrolidinyl-2-methyl or azetidinyl, each substituted by $R_8$ as defined above, (3) when A is a group of formula II wherein Y is —$NR_3$—, —O— or —S—, $R_3$ is as defined above, and the free valence is in position 7 and B is —NH—, then D is other than a group of formula V, X or XI, (4) when A is a group of formula II wherein Y is —$NR_3$—, $R_3$ is as defined above and wherein $R_1$ is in position 3 and is hydroxy or alkoxy, the free valence is in position 2 and B is —NH—, then D is other than a group of formula XII which is pyrrolidinyl-2-methyl substituted by $R_8$ as defined above, and (5) when A is a group of formula II wherein Y is —$NR_3$—, $R_3$ is as defined above and wherein $R_1$ is in position 2 and is chlorine, bromine or substituted amino, the free valence is in position 3 and B is —O—, then D is other than a group of formula XII which is a radical of formula —$(CH_2)_q$—T wherein q is 0 or 1 and T is a 5 or 6 membered heterocyclic ring containing a nitrogen ring hetero atom, their acid addition salts and quaternary ammonium salts, hereinafter referred to as compounds of the invention.

A number of the compounds excluded from the above scope have been described as pharmaceuticals e.g. dopamine antagonists or anti-emetics, but none have been described as having serotonin-M antagonist activity.

Such compounds have been disclosed in respect of the provisos for example in the following representative publications:

(1) European Patent Publication 13138 and 94742, USP 2,748,134, DOS 2803651
(2) J.Med.Chemistry, 1978, 21, p.628 and 1982 25, p. 145 DOS 2434547
(3) World Patent 84/03281
(4) Belgian Patent 701023
(5) DOS 2557342 and 2557341

None of these publications specifically disclose or suggest the present compounds.

Any alkyl moiety preferably is methyl, ethyl or propyl. Alkoxy is preferably methoxy or ethoxy. Aralkyl is conveniently aryl$(C_{1-4})$alkyl. Alkenyl is preferably allyl or methallyl. Any aryl moiety is preferably unsubstituted phenyl or phenyl mono- or poly-substituted by $(C_{1-4})$alkyl, e.g. methyl, halogen, e.g. fluorine, hydroxy, or $(C_{1-4})$alkoxy, e.g. methoxy. Preferably any substituted aryl group is mono-substituted. Aralkyl is conveniently benzyl. Halogen is fluorine, chlorine, bromine or iodine.

A is conveniently a group of formula II. In the group of formula II, the group —CO— may be attached to the ring carbon atom in position 2,3,4,5,6 or 7 of the nucleus, but preferably in position 4 and 5. Most preferably the —CO— group is attached to the ring containing Y, especially in position 3. Preferably A is indole.

$R_2$ is attached to the ring carbon atom in position 4,5,6 or 7 of the nucleus, preferably position 5 and $R_1$ is attached to the ring carbon atom in position 2 or 3 of the nucleus. Tautomers are also covered by formula I e.g. when $R_1$ is hydroxy or mercapto in the 2 position. $R_3$ is conveniently hydrogen or alkyl.

The groups of formula IV to XII may contain at least one asymmetric carbon atom e.g. those marked * which may exist in different configurations and exist in different stereoisomeric forms. The compounds may exist in racemic or optically active form.

$R_8$ is preferably alkyl especially methyl.

One preferred group of compounds comprises compounds of formula Ip

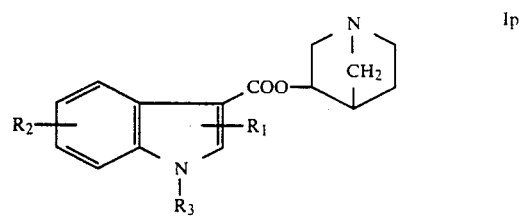

or salts thereof.

Another preferred group of compounds comprises compounds of formula Iq

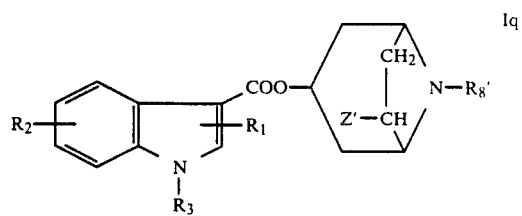

wherein
$R_8'$ is $(C_{1-4})$alkyl and
$Z'$ is methoxy.

Preferred groups of formula III are of formula IIIa

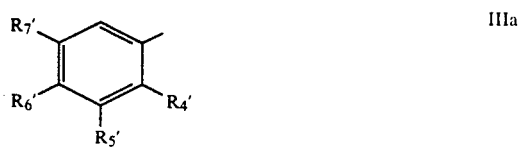

wherein $R_4'$ is $(C_{1-4})$alkoxy, especially methoxy, $R_5'$ is hydrogen, $R_6'$ is amino or $(C_{1-4})$alkylamino, especially methylamino and $R_7'$ is halogen, especially chlorine.

Of the compounds of formula I, the compounds having the group XII are preferred especially one of those wherein (a) m=2, n=0, o=0, p=1,$R_9,R_{10}$, $R_{11},R_{12}$=H and $R_8$=$CH_3$, (b) m=2, n=0, o=1, p=0,$R_9,R_{10},R_{11}$, $R_{12}$=H and $R_8$=$CH_3$, (c) m=1, n=1, o=1, p=0,,$R_9,R_{10}$, $R_{11},R_{12}$=H and $R_8$=$CH_3$, (d) m=0, n=1, o=1, p=0, $R_9,R_{10},R_{11},R_{12}$=H and $R_8$=$CH_3$, (e) m=0, n=1, o=1, p=0, $R_9,R_{10},R_{11},R_{12}$=H and $R_8$=$CH_3$, (f) m=2, n=0, o=0, p=1,$R_9$, $R_{10}$,$R_{11}$,$R_{12}$=H and $R_8$=$CH_3$,
(g) m=0, n=1, o=1, p=1,
(h) m=1, n=0, o=1, p=0,
(i) m=2, n=1, o=1, p=0,
(j) m=1, n=0, o=1, p=0.

When D is a group of formula IV to XI, these can exist in two different configurations. i.e.

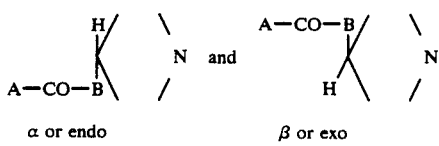

α or endo        β or exo

The two different configurations may be appreciated by making the groups have a configuration wherein a reference plane may be drawn through the carbon atoms of the ring and the nitrogen atom is above the plane and the alkylene bridge is below the plane. A group of formula IV to XI has the α configuration when the group A—CO—B— is below the plane on the same side as the alkylene bridge. This corresponds to the endo configuration and also to the configuration in tropine etc. A group of formula IV to XI has the β-configuration when it is above the plane on the same side as the nitrogen bridge. This corresponds to the exo configuration and also the configuration in pseudotropine etc. Used hereinafter is the exo/endo nomenclature. The endo isomers are preferred.

When D is a group of formula XII, this can exist in two different configurations: e.g.

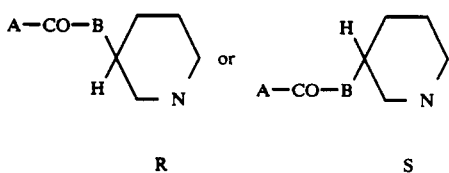

R          S

In particular the present invention provides a process for the production of a compound of formula I as well as acid addition salts thereof or quaternary ammonium salts thereof which includes the step of
(a) condensing an appropriate compound of formula XIII

     XIII wherein
A is as defined above,
a reactive derivative thereof,
or a precursor of the acid or derivative,
with an appropriate compound of formula XIV

     XIV wherein
B and D are as defined above,
or a precursor of the compound or,
(b) alkylating a compound of formula I having a secondary amino group to produce a compound of formula I with a tertiary amino group,
(c) deprotecting any protected form of a compound of formula I to obtain a compound of formula I,
(d) halogenating a compound of formula I wherein A is a group of formula II and $R_1$ is hydrogen to obtain the corresponding compound wherein $R_1$ is halogen, or
(e) alkoxylating a compound of formula I wherein A is a group of formula II and $R_1$ is halogen to obtain the corresponding compound wherein $R_1$ is alkoxy, and recovering the resultant compound of formula I as such or as acid addition salt or as a quaternary ammonium salt thereof.

It is assumed that in all these reaction processes the configuration of the groups of formulae IV to XII remains unchanged.

The condensation process of the invention to obtain amides and esters may be effected in conventional manner for analogous compounds.

For example, the carboxylic acid group may be activated in the form of a reactive acid derivative, especially for the production of amides. Suitable reactive acid derivatives may be formed as in situ as intermediates by reaction with N,N'-carbonyl-diimidazole or with N-hydroxy-succinimide. Alternatively an acid chloride may be used, e.g. produced by reaction with oxalyl chloride. In the case of sulphonic acids, the acid chloride is preferably used.

For production of esters, the alcohol may be used e.g. in the form of an alkali metal salt, preferably the lithium salt. Such salts may be produced in conventional manner, e.g. by reaction of a n-butyl lithium with the alcohol in tetrahydrofuran. If desired a heterocyclic or tertiary amine, e.g. pyridine or trietylamine, may be present, especially for the production of amides.

Suitable reaction temperatures may be from about −10° to about 100°. Higher temperatures are preferably used for amides and for groups of formula IV and VIII.

Other suitable inert organic solvents include, e.g. tetrahydrofuran or dimethoxyethane.

The compounds of the invention may be converted into other compounds of the invention, e.g. in conventional manner. Some interconversions are exemplified in processes (b),(c),(d) and (e).

The alkylation reaction or process (b) may be effected in conventional manner. Any free amino group may be alkylated, especially compounds of formula II wherein Y is NH. Appropriate alkylation conditions include reaction with an alkyl halide in the presence of a sodium alcoholate. Suitable temperatures may be from about −50° to about −30° C.

The deprotection reaction of process (c) is specifically suitable for the production of compounds with secondary amino groups, e.g. $R_8$=H or primary amino groups, e.g. $R_2$=NH2.

For example a compound of formula I may be produced in protected form, e.g. $R_8$ being replaced by a secondary amino protecting group such as benzyl. The benzyl group may be split off in conventional manner, e.g. by hydrogenation to produce the corresponding compound of formula I wherein $R_8$ is hydrogen. Suitably the hydrogenation may be effected in the presence of a palladium on active charcoal at room temperature or at a slightly elevated temperature. Suitable solvents include acetic acid, ethyl acetate or ethanol.

A primary amino group $R_1$ or $R_2$ may be protected by e.g. N-benzyloxycarbonyl. This group may be split off by hydrogenation analogously to that indicated above. In the presence of a benzyl group the N-benzyloxycarbonyl group is generally split off first so that this group may be selectively split off.

Also the amino group may be in the form of a nitro group. This can be selectively reduced in conventional manner, e.g. by iron in hydrochloric acid.

Halogenation according to process (d) may be effected in conventional manner. For example with N-chloro-succinimide may lead to chlorination. Such reactions may be effected in a suspension in chloroform.

Replacement of reactive halogen groups according to process (e) may be effected in conventional manner, e.9. by reaction with an appropriate alcohol at e.g. room temperature from 10 to 20 hours at least.

A precursor of a starting material may be employed if desired. Such a precursor may be capable of being converted into the starting material in conventional manner but instead the process of the invention is carried out with the precursor and the other starting material or materials or a precursor thereof. The resultant product is converted into the compound of the invention in conventional manner, e.g. by using the same reaction conditions by which the precursor may be converted into the starting material. Typical precursors include protected forms of a starting material, e.g. wherein amino groups are temporarily protected.

The compounds of the invention may be isolated and purified in conventional manner. If isomeric mixtures of starting materials containing groups of formula XIV are used, then the final compounds may be purified by e.g. column chromatography.

Free base forms of compounds of the invention may be converted into salt forms. For example acid addition salts may be produced in conventional manner by reacting with a suitable acid, and vice versa. Suitable acids for salt formation include hydrochloric acid, malonic acid, hydrobromic acid, maleic acid, malic acid, fumaric acid, methanesulphonic acid, oxalic acid, and tartaric acid. Quaternary ammonium salts of the compounds of the invention may be produced in conventional manner, e.g. by reaction with methyl iodide.

Insofar as the preparation of any particular starting material is not specifically described these are known or may be prepared in conventional manner.

In the following examples all temperatures are in degrees Centigrade and are uncorrected.

In the tables
(1)=decomposition
FUM=base-demifumarate
(2) Stereochemistry 1S*, 3r*,5R* , 6R*
Hygfum=hydrogenfumarate

EXAMPLE 1

1H-indol-3-yl-carboxylic acid-(3R*,4S*)-1-azabicyclo-[2.2.1]hept-3-yl-ester (exo form)

(Compound of formula I, wherein A=group of formula II, Y=—$NR_3$—, $R_1=R_2=R_3$=H, Carboxyl group in position 3, B=—O—, D=group of formula IV configuration:exo)

450 mg (4 mM) 1-azabicyclo[2.2.1]heptan-3-ol are treated dropwise with 4mM butyl lithium dissolved in hexane. The mixture is stirred for 1 hour at room temperature (25° C.). The volume is concentrated to half.

The mixture is diluted with 10 ml dimethylformamide and treated with 1.69 g indol-3-yl carboxylic acid imidazolide (obtained in conventional manner by treating N,N'-carbonyl-imidazole with indol-3-yl carboxylic acid in dry tetrahydrofuran). The resultant solution is maintained at 50° for 12 hours and then partitioned between 1 N aqueous sodium carbonate and methylene chloride. The organic phase is washed with water and concentrated to give 1.2 g of a white foam, which is chromatographed on a fifty-fold amount of silicagel using as eluant methylene chloride containing 5% methanol and 0.2% aqueous ammonia.

After 550 mg side products the title compound is eluted. The title compound is recrystallized from methylene chloride/hexane M.pt 181°–183° (decomposition).

In analogous manner the following compounds of formula I are produced:

| Example | | Formula II | | | Position of carbonyl group | B | Configuration | D = Group of formula | $R_8$ | M. pt. (°C.) | Form |
|---|---|---|---|---|---|---|---|---|---|---|---|
| | | $R_1$ | $R_2$ | Y | | | | | | | |
| 2 | | H | H | —NH— | 3 | —O— | endo | XI (Z = $OCH_3$) | $CH_3$ | 90–92 | Hygfum. |
| 3 | | H | H | —NH— | 3 | —O— | (endo) | X (1 = 3) | $CH_3$ | 176–8 | Base |
| 4 | | H | H | —NH— | 3 | —O— | endo | V | $CH_3$ | 184–5 | Base |
| 5 | | H | H | —NH— | 3 | —O— | (endo) | X (1 = 2) | $CH_3$ | 189–90 | Base |
| 6 | | H | H | —NH— | 3 | —O— | (exo) | X (1 = 3) | $CH_3$ | 209–10[(1)] | Base |
| 7 | | H | H | —NH— | 3 | —O— | endo | IV | — | 266–268 | Hydrochloride |
| 8 | | H | H | —NH— | 3 | —O— | exo | VII (t = 1) | $CH_3$ | 192–3[(1)] | Base |
| 9 | (−) | H | H | —NH— | 3 | —O— | endo | V | $CH_3$ | 195–197 | Base |
| 10 | (+) | H | H | —NH— | 3 | —O— | endo | V | $CH_3$ | 190–94 | Base |
| 11 | | H | H | —NH— | 3 | —O— | endo | VI | $CH_3$ | 140–48 | FUM |
| 12 | | H | H | —NH— | 5 | —O— | endo | XI (Z = $OCH_3$) | $CH_3$ | 155–58 | Hydrochloride |

| Example | Formula III | | | | B | Conf. | D = Group of formula | $R_8$ | M. pt. (°C.) | Form |
|---|---|---|---|---|---|---|---|---|---|---|
| | $R_4$ | $R_5$ | $R_6$ | $R_7$ | | | | | | |
| 13 | $OCH_3$ | H | $NHCH_3$ | Cl | NH | exo | IV | — | 254–55 | Hdyrochloride |
| 14 | $OCH_3$ | H | $NHCH_3$ | Cl | NH | endo | IV | — | 237–38[(1)] | Hydrochloride |

( ) = Ring is in chair form

EXAMPLE 15

(−)-1H-indolyl-3-carboxylic acid 2S-(1-methyl-2-pyrrolidinyl-methyl) ester (Compound of formula I, A=group of formula II, Y=—$NR_3$—, $R_1=R_2=R_3$=H, carbonyl group in position 3, B=—O—, D=group of formula XII, wherein o=n=0, m=2, $R_8=CH_3$, $R_9=R_{10}$=H, p=1, configuration: S)

(a) N-Methoxycarbonyl-L-proline 57.5 g L-Proline are suspended in 300 ml pyridine and the resultant suspension added dropwise from 0° to 7° within 1 hour to a mixture of 39 ml chloroformic acid methyl ester and 30 ml of absolute methylene chloride. After finishing the addition an almost clear solution results which is allowed to stand over night at room temperature. The mixture is cooled to 0°-5°. An approximately 10% hydrochloric acid solution is added until the mixture has a pH value of 1. The mixture is extracted 5 times with methylene chloride. The organic phases are combined, washed with water once, dried carboxylic acid chloride in 20 ml tetrahydrofuran at 10° to 16°. The resultant solution changes to a beige suspension which is allowed to stand for 4 hours. The mixture is partitioned between methylene chloride and an aqueous 1N sodium carbonate solution. The organic phase is evaporated to give a crystalline residue which is recrystallized once from ethyl acetate and once from methylene chloride/methanol to give the title compound.

M.pt. 162°-163° (decomp), $[\alpha]_D^{20} = -30.0°$, (c=0.85 ethanol).

In analogous manner (either via the acid chloride or the imidazolide) the following compounds of formula I are prepared.

| Example | Formula II | | | group position | B | Conf. | Formula XII | | | | | | | | | M. pt. | Form |
|---|---|---|---|---|---|---|---|---|---|---|---|---|---|---|---|---|---|
| | $R_1$ | $R_2$ | Y | | | | $R_8$ | $R_9$ | $R_{10}$ | $R_{11}$ | $R_{12}$ | m | n | o | p | | |
| 16 | H | H | —NH— | 3 | —O— | R | $CH_3$ | H | H | — | — | 2 | 0 | 0 | 1 | 163-4[1] | Base |
| 17 | H | H | —NH— | 3 | —O— | RS | $CH_3$ | H | H | H | H | 1 | 0 | 1 | 0 | 185-6 | Base |
| 18 | H | H | —NH— | 3 | —O— | RS | $CH_3$ | H | H | H | H | 0 | 1 | 1 | 1 | 140-2 | Base |
| 19 | H | H | —NH— | 3 | —O— | RS | $CH_3$ | H | H | H | H | 2 | 0 | 1 | 0 | 183-4 | Base |
| 20 | H | H | —NH— | 3 | —O— | RS | $CH_3$ | H | H | H | H | 1 | 1 | 1 | 0 | 216-7[1] | Base |
| 21 | H | H | —NH— | 3 | —O— | RS | H | $CH_3$ | $CH_3$ | $CH_3$ | $CH_3$ | 1 | 1 | 1 | 0 | 281-3[1] | FUM. |
| 22 | H | H | —NH— | 3 | —O— | RS | $CH_3$ | H | H | H | H | 2 | 1 | 1 | 0 | 141-2 | Base |
| 23 | H | H | —NH— | 3 | —NH— | RS | H | H | H | H | H | 1 | 0 | 1 | 0 | 230-1 | Base |
| 24 | H | H | —NH— | 3 | —NH— | RS | $CH_3$ | H | H | H | H | 1 | 0 | 1 | 0 | 206-7 | Base |

| Example | Formula III | | | | B | Conf. | Formula XII | | | | | | | | | M. pt. | Form |
|---|---|---|---|---|---|---|---|---|---|---|---|---|---|---|---|---|---|
| | $R_4$ | $R_5$ | $R_6$ | $R_7$ | | | $R_8$ | $R_9$ | $R_{10}$ | $R_{11}$ | $R_{12}$ | m | n | o | p | | |
| 25 | $OCH_3$ | H | $NH_2$ | Cl | NH | RS | H | H | H | H | H | 1 | 0 | 1 | 0 | 165[1] | HOX |
| 26 | $OCH_3$ | H | $NHCH_3$ | Cl | NH | RS | $CH_3$ | H | H | H | H | 0 | 1 | 1 | 1 | 196-98 | Hydrochloride | over sodium sulphate and concentrated twice by evaporation after the addition of toluene. The resultant heading compound is obtained in a form of a colourless solid which is dried at room temperature in a high vacuum. $[\alpha]_D^{20} = -145°$ (c=2.8 in water).

(b) (—)-2-hydroxymethyl-N-methyl-pyrrolidine 46 g lithium aluminium hydride are suspended in 500 ml tetrahydrofuran. A solution of 52 g N-methoxycarbonyl-L-proline in 500 ml tetrahydrofuran is added to the resultant suspension at 20° to 35° C. The mixture is heated to reflux temperature and refluxed for 24 hours. The mixture is then cooled to —10° and carefully treated dropwise with a mixture of 125 ml water and 125 ml tetrahydrofuran at —10 to 0°.

The mixture is allowed to react at room temperature and forms a white suspension. The white suspension is filtered off and the filter residue extracted three times with methylene chloride. The extracts are combined with the filtrate. The mixture is concentrated under a vacuum at 50° to give 32 g of an oil. This oil is distilled (17 mm Hg) under water vacuum.

1. Fraction 70°/17 mm=500 mg[n]$D_{20}$=1.4665
2. Fraction 72°/17 mm=4.4 g[n]$D_{20}$=1.4670
3. Fraction 75°/17 mm=750 mg[n]$D_{20}$=1.4680
4. Fraction 80°-85°/17 mm=400 mg[n]$D_{20}$=1.4680

The 2nd Fraction contains the heading compound $[\alpha]_D^{20} = -51.9°$ (c=1.65 in ethanol).

(c) (—)-1H-indol-3-yl carboxylic acid -2S-(1-methyl-2-pyrrolidinylmethyl) ester 3.45 g (—)-2-hydroxymethyl-N-methyl-pyrrolidine is dissolved in tetrahydrofuran and 18.7 ml butyl lithium in hexane is added at 10° to 18° The resultant white suspension is stirred for 45 minutes at room temperature and concentrated in a water vacuum at 17 mm Hg to a volume of about 20 ml. After addition of 15 ml tetrahydrofuran the mixture is treated with 45 g indol-3-yl The compounds of the invention exhibit pharmacological activity and are therefore useful as pharmaceuticals, e.g. for therapy.

In particular the compounds exhibit serotonin M receptor antagonist activity as indicated in standard tests. For example, in one test the action of the compounds in inhibiting the action of serotonin in reducing the amplitude of the compound action potential from the isolated rabbit vagus nerve was observed according to the principles of Riccioppo Neto, European Journal of Pharmacology (1978) 49 351-356, under conditions permitting differentiation between action potentials generated in myelinated nerve fibres (A fibres) and those generated in small non-myelinated fibres (C fibres) as described by B.Oakley and R.Schater, Experimental Neurobiology, A Laboratory Manual, University of Michigan Press, 1978, p.85 to 96. Serotonin itself exerts its effect selectively on the C-f bres progressively with dosage. This action of serotonin is not blocked by the known serotonin antagonists, metitepine, methysergide, BOL—148, which have been said to block D receptors for serotonin, but not M receptors (see Gaddam and Picarlli, Brit.J.Pharmacol. (1957), 12, 323-328). It therefore appears that serotonin reduces the amplitude of the action potential carried by the C fibres through an effect mediated by M receptors for serotonin which are located on these nerve fibres.

The test may be effected by establishing a dose response curve for serotonin ($10^{-7}-5\times10^{-6}$ M) after setting up the nerve. The serotonin is washed out and when the C fibre action potential has regained its original amplitude the compound of the invention at a set concentration of from about $10^{-10}$ M to about $10^{-6}$ M is preincubated with the nerve for 30 to 60 minutes. Varying concentrations of serotonin ($10^{-7}$ to $10^{-4}$ M) are then applied with the compound of the invention at the concentration as was present during the preincubation period.

The M receptor antagonists of the invention either entirely block the action of serotonin (non-competitive antagonist) or cause a Parallel shift of the serotonin/dose response curve to the right (i.e. increased concentrations of serotonin were required for effect) (competitive antagonist). The $pD'_2$ or $pA_2$ value may be obtained in the conventional manner.

The serotonin M receptor antagonist activity is also indicated by inhibiting the effect of serotonin on the isolated rabbit heart according to the method of J.R.Fozard and A.T.Moborak Ali, European Journal of Pharmacology, (1978), 49, 109–112 at concentrations of $10^{-11}$ to $10^{-5}$ M of the compound of the invention. $pD'_2$ or $pA_2$ values may be calculated in the conventional manner.

The action of the compounds as serotonin M receptor antagonists for the treatment of analgesia is confirmed by action in the hot Plate test at a dose of from about 0.1 to 100 mg/kg s.c. or p.o.

The serotonin M receptor antagonist activity is furthermore indicated in the cantharidine blister base test at a concentration of about $10^{-8}$ M. A blister is produced on the skin of the forearm of human volunteers with cantharidine. When serotonin is applied to the base of such blisters it produces pain which can be measured, the intensity being proportional to the concentration of serotonin applied. The procedure has been described by C. A. Keele and D. Armstrong in Substances producing Pain and Itch, Edward Arnold, London, 1964, p. 30 to 57. This algesic action of serotonin is not inhibited by the serotonin D receptor antagonists such as lysergic acid diethylamide or its bromo derivative and is therefore believed to be mediated by M receptors.

In the procedure followed the area under the curve instead of the peak amplitude is measured by a linear integrater coupled to a pain intensity indicator which is operated by the volunteer. With increasing concentrations of serotonin a cumulative dose-response curve to serotonin may be obtained. When no further response on increasing the serotonin concentration is obtained, the serotonin is washed off and the blister incubated with physiological buffer solution for at least 40 minutes before the compound of the invention is applied. The test substance is preincubated with the blister base for 30 minutes at a concentration of about $10^{-8}$ M before varying concentrations of serotonin are applied. A $pA_2$ value may be obtained in the conventional manner.

The compounds of the invention are useful as serotonin M receptor antagonists, e.g. for the treatment of pain, especially migraine, vascular and cluster headaches and trigeminal neuralgia and also for the headaches of heart circulation disorders, e.g. for the treatment of sudden death, and possibly as anti-psychotics.

The compounds of the invention furthermore exhibit antiarrhythmic activity as indicated by their serotonin M receptor antagonist activity and in standard tests. For example the compounds inhibit arrhythmias induced by norepinerphrine in anaesthetized rats. In this test infusions of norepinerphrine (3 to 10 microgram/animal body weight) are given until an arrhythmic phase as indicated by ECG measurements lasts longer than 10 seconds duration. After control of 3 consecutive injections of norepinerphrine the compound of the invention is injected at from about 10 to about 500 microgram/kg animal body weight followed by norephinerphrine injections. The arrhythmic phase is reduced, or abolished depending on the dose of test compound.

The compounds are therefore useful as anti-arrhythmic agents.

For these uses the dosage will, of course, vary depending on the compound employed, mode of administration and treatment desired. However, in general, satisfactory results are obtained when administered at a daily dosage of from about 0.1 mg to about 40 mg per kg animal body weight, conveniently given in divided doses 2 to 4 times a day or in sustained release form. For the larger mammals, the total daily dosage is in the range from about 0.5 to about 500 mg, and dosage forms suitable for oral administration comprise from about 0.2 mg to about 250 mg of the compounds admixed with a solid or liquid pharmaceutical carrier or diluent.

The compounds of formula I may be administered in similar manner to known standards for use in these utilities. The suitable daily dosage for a particular compound will depend on a number of factors such as its relative potency of activity. It has for example been determined in the above heart test that the preferred compound of the invention, Example 2 has a $pA_2$ of 11. It is therefore indicated that this compound would be administered as an anti-arrhythmic at a daily dose of from 50 to 100 mg.

The present invention accordingly provides a compound of the invention in pharmaceutically acceptable form, e.g. in free base form, or pharmaceutically acceptable acid addition salt form or quaternary ammonium salt form, for use as a pharmaceutical, particularly for use as a serotonin M antagonist for those diseases where blockage of serotonin M receptors would be expected to have beneficial effects, e.g. as an analgesic agent, especially as an anti-migraine agent and as an anti-arrhythmic agent.

The compounds of the invention may be administered in free base form, or in pharmaceutically acceptable salt form, e.g. suitable acid addition salts and quaternary ammonium salts. Such salts exhibit the same order of activity as the free bases. The present invention accordingly also provides a pharmaceutical composition comprising a compound of the invention, in free base form or an acid addition salt thereof or a quaternary ammonium salt thereof, in association with a pharmaceutical carrier or diluent. Such compositions may be formulated in conventional manner so as to be for example a solution or a tablet.

The preferred compound is the title compound of Example 15.

A preferred group of compounds is these wherein A is a group of formula II wherein $R_1$ and $R_2$ independently are hydrogen, halogen, $(C_{1-4})$alkyl or $(C_{1-4})$alkoxy, $R_2$ is in position 4 or 5, $R_3$ is hydrogen or $(C_{1-4})$alkyl and the free bond is in position 3,4 or 5. Another preferred group of compounds are those wherein A is a group of formula III wherein $R_4$ is hydrogen, halogen or $(C_{1-4})$alkoxy, $R_5$ is hydrogen or halogen or $(C_{1-4})$alkoxy, $R_6$ is amino, nitro, $(C_{1-4})$alkylamino, di$(C_{1-4})$alkylamino, halogen or 1-pyrrolyl and $R_7$ is hydrogen or halogen.

In a group of compounds A is a group of formula II wherein $R_1$ and $R_2$ independently are hydrogen, Y is —NH— and the free bond is in position 3, or a group of formula III wherein $R_4$ is $(C_{1-4})$alkoxy, $R_5$ is hydrogen, $R_9$ is amino or alkylamino, $R_7$ is halogen, and D is a group of formula IV, V, VI, VII wherein t is 1, X, XI or XII wherein n,m,o and p is 0 or 1, and wherein $R_8$ is hydrogen or $(C_{1-4})$alkyl.

In one group of compounds D is a group of formula IV to XI. In another group of compounds D is a group of formula XII.

Conveniently when A is a group of formula III and B is NH then at least one of $R_4$ to $R_7$ is alkylamino. Conveniently D is a group of formula IV or XII.

In a 1st group of compounds Y is —$CH_2$—.
In a 2nd group of compounds Y is —$NR_3$—.
In a 3rd group of compounds Y is —O—.
In a 4th group of compounds Y is —S—.
In a 5th group $R_1$ or $R_2$ is hydrogen.
In a 6th group $R_1$ or $R_2$ is halogen.
In a 7th group $R_1$ or $R_2$ is alkyl.
In an 8th group $R_1$ or $R_2$ is alkoxy.
In a 9th group $R_1$ or $R_2$ is hydroxy.
In a 10th group $R_1$ or $R_2$ is amino.
In an 11th group $R_1$ or $R_2$ is alkylamino.
In a 12th group $R_1$ or $R_2$ is alkylamino.
In a 13th group $R_1$ or $R_2$ is mercapto.
In a 14th group $R_1$ or $R_2$ is alkylthio.
In a 15th group $R_3$ is hydrogen.
In a 16th group $R_3$ is alkyl.
In a 17th group $R_3$ is alkenyl.
In an 18th group $R_3$ is aryl.
In a 19th group $R_3$ is arylalkyl.
In a 20th group one of $R_4$ to $R_7$ is hydrogen.
In a 21st group one of $R_4$ to $R_7$ is amino.
In a 22nd group one of $R_4$ to $R_7$ is nitro.
In a 23rd group one of $R_4$ to $R_7$ is alkylamino.
In a 24th group one of $R_4$ to $R_7$ is alkylamino.
In a 25th group one of $R_4$ to $R_7$ is halogen.
In a 26th group one of $R_4$ to $R_7$ is alkoxy.
In a 27th group one of $R_4$ to $R_7$ is alkyl.
In a 28th group one of $R_4$ to $R_7$ is alkanoylamino.
In a 29th group one of $R_4$ to $R_7$ is pyrrolyl.
In a 30th group of compounds B is —O—.
In a 31st group of compounds B is —NH—.
In a 32nd group $R_8$ is hydrogen.
In a 33rd group $R_8$ is alkyl.
In a 34th group $R_8$ is alkenyl.
In a 35th group $R_8$ is aralkyl.
In a 36th group D is a group of formula IV.
In a 37th group D is a group of formula V.
In a 38th group D is a group of formula VI.
In a 39th group D is a group of formula VII.
In a 40th group D is a group of formula VIII.
In a 41st group D is a group of formula IX.
In a 42nd group D is a group of formula X.
In a 43rd group D is a group of formula XI.

What we claim is:

1. A compound of formula Iq

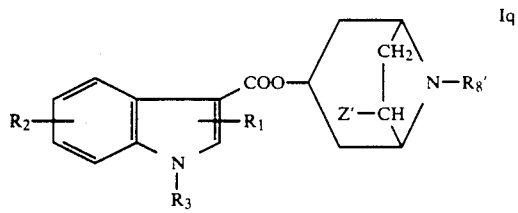

where
$R_1$ and $R_2$, independently, are hydrogen, halogen, $(C_{1-4})$alkyl, $(C_{1-4})$alkoxy, hydroxy, amino, $(C_{1-4})$alkylamino, di-$(C_{1-4})$alkylamino, mercapto or $(C_{1-4})$alkylthio;

$R_3$ is hydrogen, $(C_{1-4})$alkyl, $(C_{1-4})$alkenyl, aryl or aralkyl;

$Z'$ is methoxy; and $R_{8'}$ is $(C_{1-4})$alkyl;

or a pharmaceutically acceptable acid addition or quaternary ammonium salt thereof.

2. A pharmaceutical composition useful for inducing a serotonin M receptor antagonist effect comprising a pharmaceutically acceptable carrier or diluent and a therapeutically effective amount of a compound of claim 1, or a pharmaceutically acceptable acid addition or quaternary ammonium salt thereof.

3. A method of inducing a serotonin M receptor antagonist effect comprising administering to a subject in need of such treatment a therapeutically effective amount of a compound of claim 1, or a pharmaceutically acceptable acid addition or quaternary ammonium salt thereof.

4. A method of treating algesia by inducing a serotonin M receptor antagonist effect comprising administering to a subject in need of such treatment a therapeutically effective amount of a compound of claim 1, or a pharmaceutically acceptable acid addition or quaternary ammonium salt thereof.

5. A method of treating heart circulation disorders by inducing a serotonin M receptor antagonist effect comprising administering to a subject in need of such treatment a therapeutically effective amount of a compound of claim 1, or a pharmaceutically acceptable acid addition or quaternary ammonium salt thereof.

6. A method of treating arrhythmia by inducing a serotonin M receptor antagonist effect comprising administering to a subject in need of such treatment a therapeutically effective amount of a compound of claim 1, or a pharmaceutically acceptable acid addition or quaternary ammonium salt thereof.

* * * * *